United States Patent
Payne

(10) Patent No.: US 9,138,189 B1
(45) Date of Patent: Sep. 22, 2015

(54) EARPLUG WITH THERMOCHROMIC PROBE AND STEM FOR INDICATING UNSAFE CORE BODY TEMPERATURE

(71) Applicant: Marisela Payne, Baytown, TX (US)

(72) Inventor: Marisela Payne, Baytown, TX (US)

(*) Notice: Subject to any disclaimer, the term of this patent is extended or adjusted under 35 U.S.C. 154(b) by 95 days.

(21) Appl. No.: 13/854,085

(22) Filed: Mar. 30, 2013

Related U.S. Application Data

(60) Provisional application No. 61/686,157, filed on Apr. 2, 2012.

(51) Int. Cl.
- *A61B 5/00* (2006.01)
- *A61B 5/01* (2006.01)
- *A61F 11/08* (2006.01)

(52) U.S. Cl.
CPC ............... *A61B 5/6817* (2013.01); *A61B 5/01* (2013.01); *A61B 5/74* (2013.01); *A61F 11/08* (2013.01)

(58) Field of Classification Search
CPC .................................................. A61B 5/6817
USPC ........................... 600/549; 374/162, E13.002
See application file for complete search history.

(56) References Cited

U.S. PATENT DOCUMENTS

| | | | |
|---|---|---|---|
| 5,333,622 A | 8/1994 | Casali et al. | |
| 6,450,970 B1* | 9/2002 | Mahler et al. | 600/549 |
| 6,622,816 B2 | 9/2003 | Falco et al. | |
| 6,773,405 B2 | 8/2004 | Fraden et al. | |
| 2010/0268112 A1* | 10/2010 | Short et al. | 600/549 |

* cited by examiner

*Primary Examiner* — Brian Szmal
(74) *Attorney, Agent, or Firm* — Kenneth A. Roddy

(57) ABSTRACT

An earplug to be worn in the ear canal of a person has a thermochromic probe and stem portion that continuously monitors the core body temperature of the wearer and changes color reversibly upon detection of temperatures above or below a temperature range considered to be normal for tympanic temperature to visually indicate to the wearer or an observer that the wearer has an unsafe core body temperature. The earplug has an outer body formed of a soft resilient material configured to conform to the generally conical interior profile of the ear canal and become resiliently and removably engaged therein when pressed into the canal. The probe has a head portion and a radial flange configured to permit a desired insertion distance such that, when properly inserted, the head portion is near, but not in contact, with the tympanic membrane and engaged on the conical wall of the ear canal.

9 Claims, 1 Drawing Sheet

EARPLUG WITH THERMOCHROMIC PROBE AND STEM FOR INDICATING UNSAFE CORE BODY TEMPERATURE

CROSS REFERENCE TO RELATED APPLICATION

This application claims priority of U.S. Provisional Patent Application Ser. No. 61/686,187, filed on Apr. 2, 2012.

BACKGROUND OF THE INVENTION

1. Field of the Invention

This invention relates generally to tympanic thermometers and, more particularly, to an earplug having a thermochromic probe and stem that continuously monitors the core body temperature of the wearer and visually displays a first color in a temperature range considered to be normal for tympanic temperature and changes color reversibly upon detection of a temperature above or below that range to visually indicate to the wearer or an observer that the wearer has an unsafe core body temperature.

2. Background Art

Normal functioning of humans requires a body temperature of approximately 98.6° F. (37° C.). Hyperthermia is defined as elevated core body temperature of greater than 100.4° F. (38° C.). Hyperthermia occurs when the body produces or absorbs more heat than it can dissipate. It is usually caused by prolonged exposure to high temperatures. Mild hyperthermia is commonly called heat exhaustion or heat prostration, which is a serious medical emergency in which the body's core temperature rises to 100.4° F. (38° C.). Workers working in hot industrial and outdoor environments, such as for example roofers, firefighters, construction and factory workers, and athletes exercising strenuously in hot climates are susceptible to heat exhaustion. Common symptoms include headache, nausea, dizziness, fatigue, irritability, and confusion. Severe hyperthermia is called heat stroke. Heat stroke may come on suddenly, but it usually follows the untreated milder stages. Heat stroke is the most serious heat related medical emergency in which the body's temperature regulating system fails and the core body temperature can rise to dangerous levels greater than 104° F. (40° C.). Symptoms of heat stroke include hot, dry skin, lack of sweating, a very fast pulse, confusion and perhaps seizures or coma. If untreated, heat stroke can lead to death or permanent disability.

Hypothermia is the opposite of hyperthermia which is present in heat exhaustion and heat stroke. Hypothermia is defined as any body temperature below 95.0° F. (35.0° C.). It is subdivided into four different degrees: mild 0.90-95° F. (32-35° C.); moderate, 82-90° F. (28-32° C.); severe, 68-82° F. (20-28° C.); and profound at less than 68° F. (20° C.). As body temperature decreases, characteristic symptoms occur such as shivering and mental confusion. In severe hypothermia, all body functions are decreased, including heart rate, breathing rate, metabolism blood pressure and mental activity. Difficulty in speaking, sluggish thinking, and amnesia start to appear; inability to use hands and stumbling is also usually present. Cellular metabolic processes shut down. Below 86° F. (30° C.), the exposed skin becomes blue and puffy, muscle coordination becomes very poor, walking becomes almost impossible, and the person exhibits incoherent/irrational behavior. If core body temperature is lower than 82° F. (28° C.), the condition is life-threatening without immediate medical attention.

The hypothalamus is located in the base of the brain and acts as the body's thermostat. It functions by monitoring heat sensors throughout the body and adjusting the temperature based on the body's needs. The goal of the hypothalamus is to maintain the body's core temperature (the temperature of the heart, lungs, liver, kidneys, brain, etc.) between 96.9° F. to 100.4° F. (36° to 38° C.). It is well recognized that the tympanic membrane within the ear canal is an excellent site for determination of the core temperature of a body due to its proximity to the external carotid artery which supplies blood to the hypothalamus. Patients show changes in core temperature at the tympanic membrane prior to peripheral sites such as the mouth or rectum.

It is well known that the tympanic region of the ear canal follows the core body temperature with high fidelity. This region includes the tympanic membrane and the adjacent walls of the ear canal. Most conventional ear thermometers, also known as aural thermometers and tympanic thermometers have a short tube or probe that is placed into the ear canal and measure the heat that is emitted from the tympanic membrane of the eardrum by means of an infrared detector on the device and a digital readout is given. Most all ear thermometers position the end of the probe or a sensor adjacent to, but not in contact with, the tympanic membrane. Generally, therefore, not the tympanic membrane temperature is taken, which is considered as being representative of the true core body temperature, but rather an intermediate value that lies between the temperature of the tympanic membrane and the ear canal temperature.

The commonly accepted average core body temperature (measured internally) is 98.6° F. (37° C.). The typical oral (under the tongue) measurement is slightly cooler, at 97.5° F. to 98.9° F. (36.4° C. to 37.2° C.), and temperatures of 95.9° F. to 99.5° F. (35.5° C. to 37.5° C.) is considered normal for tympanic temperature.

Casali et al, U.S. Pat. No. 5,333,622 discloses a custom-molded earplug for swimming protection, hearing protection, and the like, fabricated in situ by depositing a foaming material within a person's ear and allowing the foaming material to form foam. Acoustic and electronic equipment such as a Helmholtz resonator or other tuned device capable of modifying sound waves, a communications transmitter, a communications receiver, a communications transceiver, a hearing aid, an ear microphone, a personal earphone, and a hearing test transducer or probe tube can be fabricated in the ear in a similar fashion. Temperature sensing elements may also be incorporated within or positioned by the foaming material to provide an in the ear thermometer.

Fraden et al, U.S. Pat. No. 6,773,405 discloses a continuous core body temperature monitor in the form of a pliable ear plug that conforms to the shape of an ear canal and incorporates a temperature sensor that is clamped between the plug and the ear canal wall. The external surface of the plug is connected to an external temperature sensor and a heating element that compensate for a heat lost from the ear canal to the environment by maintaining the temperature gradient between the temperature sensor and the heating element close to zero.

Falco et al, U.S. Pat. No. 6,622,816 discloses earplugs wherein an energy-activated color change material is included within or on the earplug that exhibits a visual change upon exposure to thermal energy to indicate a proper fit. When inserted into a wearer's ears, the earplug interacts with the thermal energy in the interior of the ear canal and changes color creating at least two visual zones. A first zone is the color of the earplug prior to insertion and a second visual zone is the color of the earplug when it is exposed to and is absorbing thermal energy from the interior of the ear canal. The edge of the change in color will spread to at least a portion of the exterior portion of the earplug, or the entire earplug, enough to be visually apparent to an observer that a proper fit has been achieved for maximum attenuation. The '816 patent only determines a proper fit and teaches that the color change occurs when the temperature where the earplug is located is at about 50° F. to about 90° F. (about 10° C. to 32.2° C.), which is well below the normal average core body temperature considered normal for tympanic temperature of humans.

SUMMARY OF THE INVENTION

The present invention overcomes the aforementioned problems and is distinguished over the prior art in general, and these patents in particular, by an earplug having a thermochromic probe and stem portion that continuously monitors the core body temperature of the wearer and changes color to visually indicate an unsafe core body temperature. The outer body of the earplug is formed of a soft resilient material configured conform to the generally conical interior profile of the ear canal and become resiliently and removably engaged therein when pressed into the canal. The probe has a head portion and a radial flange configured to permit a desired insertion distance such that, when properly inserted, the head portion is near, but not in contact, with the tympanic membrane and engaged on the conical wall of the ear canal. The probe and stem portion includes a temperature-sensitive color-changing thermochromic additive that displays a first color at temperature ranges of 95.9° F. to 99.5° F. (35.5° C. to 37.5° C.) considered to be normal for tympanic temperature and changes color reversibly upon detection of a temperature above or below that range to visually indicate to the wearer or an observer that the wearer has an unsafe core body temperature. The color may reversibly change to the second color upon detection of a temperature of about 100° F. (37.7° C.) within the ear canal to indicate an unsafe hyperthermic condition, and/or upon detection of a temperature of about 95.0° F. (35.0° C.) to indicate an unsafe hypothermic condition.

One of the significant features and advantages of the present invention is that it provides a visual indication of an unsafe core body temperature condition of the wearer.

Another feature and advantage of the present invention is that the earplug can be easily positioned securely and reliably in the wearer's ear canal.

Another feature and advantage of the present invention is that the earplug and its probe are configured to be automatically secured at proper distance in the ear canal.

Another feature and advantage of the present invention is that the earplug and its probe are configured to place the head portion of the probe near, but not in contact, with the tympanic membrane such that it engages the conical wall of the ear canal.

Another feature and advantage of the present invention is that the earplug can be worn comfortably for long periods of time to continuously monitor the core body temperature of the wearer in hot working environments and during strenuous exercise in hot climates, or in cold working environments and during activities in cold climate conditions.

Further features and advantages of the present invention is that it is simple in construction, inexpensive to manufacture, and rugged and reliable in operation.

Other features and advantages of the invention will become apparent from time to time throughout the specification and claims as hereinafter related.

DESCRIPTION OF THE PREFERRED EMBODIMENT

Figure 1:
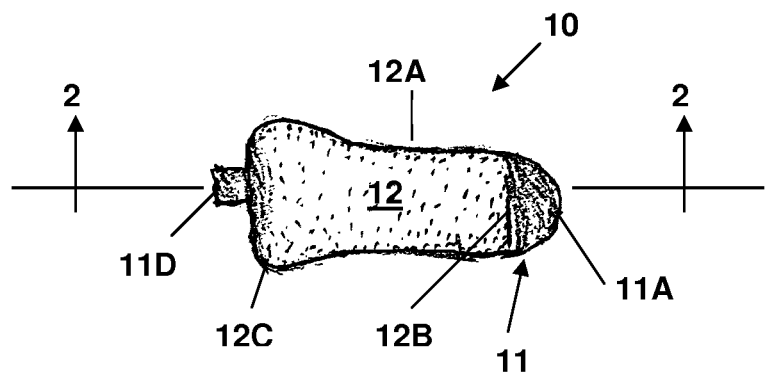
FIG. 1 is a side elevation view of the earplug in accordance with the present invention.
Figure 2:
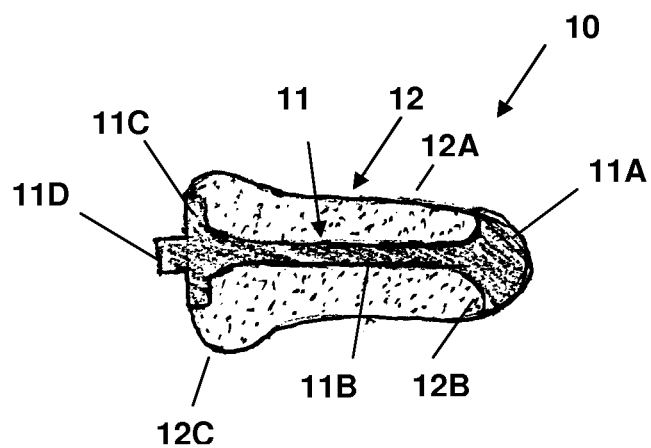
FIG. 2 is a longitudinal cross section view of the earplug, taken along line 2-2 of FIG. 1.

Referring to the drawings by numerals of reference, there is shown in FIGS. 1 and 2, a preferred earplug 10. The earplug 10 includes a probe 11 encircled by an outer body 12 that is shaped to be removably received in the ear canal of a wearer.

The probe 11 has a generally mushroom-shaped convex rounded head portion 11A, a small diameter rod-shaped intermediate portion 11B extending a distance longitudinally therefrom, an enlarged diameter radial flange portion 11C at the end of the intermediate portion, and a small diameter rod-shaped stem portion 11D extending a distance longitudinally from the radial flange portion.

The probe 11 is formed of a semi-rigid or rigid material such as, for example but not limited thereto, a plastic material. The material forming the probe 11 includes a temperature-sensitive color-changing thermochromic additive that changes color reversibly when subject to a predetermined temperature. The thermochromic constituent may be liquid crystals, a pigment, a polymer, a dye, an ink, or combinations thereof. In a preferred embodiment, the thermochromic constituent of the probe material displays a first color at temperature ranges of 95.9° F. to 99.5° F. (35.5° C. to 37.5° C.) considered to be normal for tympanic temperature and changes color reversibly upon detection of a temperature above or below that range to visually indicate to the wearer or an observer that the wearer has an unsafe core body temperature. The color may reversibly change to the second color upon detection of a temperature of about 100° F. (37.7° C.) within the ear canal to indicate an unsafe hyperthermic condition, and/or upon detection of a temperature of about 95.0° F. (35.0° C.) to indicate an unsafe hypothermic condition.

The rod-shaped intermediate portion 11B beneath the head portion 11A and the radial flange portion 11C at the end of the intermediate portion are encircled by the outer body 12, and the rod-shaped stem portion extends distance longitudinally outward from the outer body. In a preferred embodiment, the outer body 12 is formed of a resilient foam material of the type conventionally used for creating earplugs, and has a generally cylindrical main body portion 12A with a first end 12B configured to reside beneath the underside of the head portion 11A of the probe 11, and a contiguous enlarged diameter flange end portion 12C that surrounds the radial flange portion 11C of the probe. The circumference of the enlarged diameter flange end portion 12B may be outwardly rounded.

As with conventional earplugs, the exterior periphery of the outer body 12 is of a diameter slightly greater than the generally conical interior profile of the ear canal, so as to conform to the shape of the canal and become resiliently and removably engaged therein when pressed into the canal. The earplug 10 may be inserted into the ear canal by gripping the outwardly extending rod-shaped stem portion 11D of the probe between the thumb and fingers and gently pushing into the wearer's ear.

The radial flange 11C and the head portion 11A of the probe 11 are sized and shaped to permit a desired insertion distance such that, when properly inserted, the head portion of the probe is near, but not in contact, with the tympanic membrane. Thus, the head portion 11A of the probe 11 is disposed at a position adjacent to, and spaced from, the tympanic membrane and engaged on the conical wall of the ear canal, and the stem portion 11D of the probe extends a short distance outwardly from the end of the earplug body. Thus, the inserted earplug 10 continuously monitors the core body temperature of the wearer.

As discussed above, the tympanic temperature which represents the core body temperature is an intermediate value that lies between the temperature of the tympanic membrane and the ear canal temperature and temperatures of 95.9° F. to 99.5° F. (35.5° C. to 37.5° C.) is considered to be normal for tympanic temperature. The probe 11 and its stem portion 11D are a first color in that temperature range and change color reversibly upon detection of a temperature above or below that range to visually indicate to the wearer or an observer that the wearer has an unsafe core body temperature. The color may reversibly change to the second color upon detection of a temperature of about 100° F. (37.7° C.) within the ear canal to indicate an unsafe hyperthermic condition, and/or upon detection of a temperature of about 95.0° F. (35.0° C.) to indicate an unsafe hypothermic condition. Alternatively, the color change may be accomplished by a change in intensity of the color of the probe 11 and its stem portion 11D.

Although for purposes of example, the outer body 12 has been described as being formed of a resilient foam material of the type conventionally used for creating earplugs, it should be understood that it may be formed from any number of suitable materials including foams and non-foams, such as polyurethane, silicone, polyvinyl chloride foam, plasticized polymeric foams, temperature-dependent viscoelastic polymeric foams, dynamically stiff foams, rubber, polymer gels, thermoplastic elastomers, and combinations thereof. It should also be understood that the outer body 12 may have other conventional earplug shapes, such as cone-shaped, bullet-shaped, multi-flange-shaped, and the like.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. An earplug to be worn in the ear canal of a person that continuously monitors the core body temperature the wearer and changes color at temperatures below a temperature range considered to be normal for tympanic temperature to visually indicate to the wearer or an observer that the wearer has an unsafe core body temperature, comprising:

an earplug having an outer body and a thermochromic probe with a head portion at a first one end and stem portion extending therefrom and terminating at a second end;

said outer body formed of a soft resilient material encircling said probe such that said head portion and a portion of said stem portion are exposed, and having an exterior periphery configured to conform to a conical interior profile of the ear canal and become resiliently and removably engaged therein when pressed into the canal such that said head portion is disposed at a position adjacent to, and spaced from, a tympanic membrane in the ear canal and said stem portion extends a distance outwardly from an outer end of said outer body;

said probe formed of a semi-rigid or rigid material that includes a temperature-sensitive color-changing thermochromic constituent selected from the group consisting of liquid crystals, pigments, polymers, dyes, and inks that changes color reversibly when subject to a predetermined temperature; and said probe has a first color at temperature range of from 95.9° F. to 99.5° F. (35.5° C. to 37.5° C.), considered to be normal for tympanic temperature, and changes color reversibly upon detection of a temperature of 95.0° F. (35.0° C.) within the ear canal to indicate to the wearer or an observer an unsafe hypothermic condition.

2. The earplug according to claim 1, wherein said thermochromic probe has a mushroom-shaped convex rounded head portion, and said stem portion has a smaller diameter intermediate portion extending a distance longitudinally therefrom, an enlarged diameter radial flange portion disposed a distance from said head portion, and a smaller diameter stem portion extending a distance longitudinally outward from said radial flange portion sufficient to be easily visible and to be gripped between the thumb and fingers of a user to facilitate insertion into and removal from the ear canal.

3. The earplug according to claim 2, wherein said radial flange is spaced a distance from said head portion to provide an insertion distance therebetween to prevent direct contact of said head portion with the tympanic membrane such that when properly inserted into the ear canal, the head portion is near, but not in contact, with the tympanic membrane and engaged on the conical wall of the ear canal.

4. The earplug according to claim 2, wherein said outer body has a cylindrical main body portion with a first end configured to reside beneath an underside of said mushroom-shaped convex rounded head portion of said probe, and a contiguous enlarged diameter flange end portion that surrounds said radial flange portion.

5. An earplug to be worn in the ear canal of a person that continuously monitors the core body temperature the wearer and changes color at temperatures above or below a temperature range considered to be normal for tympanic temperature to visually indicate to the wearer or an observer that the wearer has-an unsafe core body temperature, comprising:

an earplug having an outer body and a thermochromic probe with a head portion at a first one end and stem portion extending therefrom and terminating at a second end;

said outer body formed of a soft resilient material encircling said probe such that said head portion and a portion of said stem portion are exposed, and having an exterior periphery configured to conform to a conical interior profile of the ear canal and become resiliently and removably engaged therein when pressed into the canal such that said head portion is disposed at a position adjacent to, and spaced from, a tympanic membrane in the ear canal and said stem portion extends a distance outwardly from an outer end of said outer body;

said probe formed of a semi-rigid or rigid material that includes a temperature-sensitive color-changing thermochromic constituent selected from the group consisting of liquid crystals, pigments, polymers, dyes, and inks that changes color reversibly when subject to a predetermined temperature; and said probe has a first color at temperature range of from 95.9° F. to 99.5° F. (35.5° C. to 37.5° C.) considered to be normal for tympanic temperature and changes color reversibly upon detection of a temperature of 100° F.

(37.7° C.) within the ear canal to indicate to the wearer or an observer an unsafe hyperthermic condition, and changes color reversibly upon detection of a temperature of 95.0° F. (35.0° C.) within the ear to indicate to the wearer or an observer an unsafe hypothermic condition.

6. The earplug according to claim 5, wherein said thermochromic probe has a mushroom-shaped convex rounded head portion, and said stem portion has a smaller diameter intermediate portion extending a distance longitudinally therefrom, an enlarged diameter radial flange portion disposed a distance from said head portion, and a smaller diameter stem portion extending a distance longitudinally outward from said radial flange portion sufficient to be easily visible and to be gripped between the thumb and fingers of a user to facilitate insertion into and removal from the ear canal.

7. The earplug according to claim 6, wherein said radial flange is spaced a distance from said head portion to provide an insertion distance therebetween to prevent direct contact of said head portion with the tympanic membrane such that when properly inserted into the ear canal, the head portion is near, but not in contact, with the tympanic membrane and engaged on the conical wall of the ear canal.

8. The earplug according to claim 7, wherein said outer body has a cylindrical main body portion with a first end configured to reside beneath an underside of said generally mushroom-shaped convex rounded head portion of said probe, and a contiguous enlarged diameter flange end portion that surrounds said radial flange portion.

9. An earplug to be worn in the ear canal of a person that continuously monitors the core body temperature the wearer and changes color at temperatures above a temperature range considered to be normal for tympanic temperature to visually indicate to the wearer or an observer that the wearer has an unsafe core body temperature, comprising:

an earplug having an outer body and a thermochromic probe with a head portion at a first one end and stem portion extending therefrom and terminating at a second end;

said probe formed of a semi-rigid or rigid material that includes a temperature-sensitive color-changing thermochromic constituent selected from the group consisting of liquid crystals, pigments, polymers, dyes, and inks that changes color reversibly when subject to a predetermined temperature;

said probe having a mushroom-shaped convex rounded head portion, and said stem portion has a smaller diameter intermediate portion extending a distance longitudinally therefrom, an enlarged diameter radial flange portion disposed a distance from said head portion, and a smaller diameter stem portion extending a distance longitudinally outward from said radial flange portion sufficient to be easily visible and to be gripped between the thumb and fingers of a user to facilitate insertion into and removal from the ear canal;

said outer body formed of a soft resilient material encircling said probe having a first end configured to reside beneath an underside of said mushroom-shaped convex rounded head portion and a contiguous enlarged diameter flange end portion that surrounds said radial flange portion of said probe such that said head portion and said smaller diameter stem portion are exposed, and having an exterior periphery configured to conform to a conical interior profile of the ear canal and become resiliently and removably engaged therein when pressed into the canal such that said head portion is disposed at a position adjacent to, and spaced from, a tympanic membrane in the ear canal and said smaller diameter stem portion extends a distance outwardly from an outer end of said outer body; and said probe has a first color at temperature range of from 95.9° F. to 99.5° F. (35.5° C. to 37.5° C.) considered to be normal for tympanic temperature and changes color reversibly upon detection of a temperature of 100° F. (37.7° C.) within the ear canal to indicate to the wearer or an observer an unsafe hyperthermic condition.

\* \* \* \* \*